US009012620B2

(12) United States Patent
Schroff et al.

(10) Patent No.: US 9,012,620 B2
(45) Date of Patent: Apr. 21, 2015

(54) DNA CONSTRUCTS FOR SPECIFIC INHIBITION OF GENE EXPRESSION BY RNA INTERFERENCE

(75) Inventors: Matthias Schroff, Berlin (DE); Detlef Oswald, Berlin (DE)

(73) Assignee: Mologen AG, Berlin (DE)

( * ) Notice: Subject to any disclaimer, the term of this patent is extended or adjusted under 35 U.S.C. 154(b) by 1323 days.

(21) Appl. No.: 12/095,062

(22) PCT Filed: Nov. 22, 2006

(86) PCT No.: PCT/DE2006/002083
§ 371 (c)(1),
(2), (4) Date: May 27, 2008

(87) PCT Pub. No.: WO2007/059760
PCT Pub. Date: May 31, 2007

(65) Prior Publication Data
US 2008/0311630 A1    Dec. 18, 2008

(30) Foreign Application Priority Data

Nov. 25, 2005  (EP) .................................. 05025727

(51) Int. Cl.
| | |
|---|---|
| *C07H 21/04* | (2006.01) |
| *C12N 15/00* | (2006.01) |
| *C12N 15/11* | (2006.01) |
| *C12N 15/113* | (2010.01) |

(52) U.S. Cl.
CPC ............ *C12N 15/111* (2013.01); *C12N 15/113* (2013.01); *C12N 2310/111* (2013.01); *C12N 2310/14* (2013.01); *C12N 2310/52* (2013.01); *C12N 2310/53* (2013.01); *C12N 2330/30* (2013.01)

(58) Field of Classification Search
USPC ...................................... 536/24.5; 435/320.1
See application file for complete search history.

(56) References Cited

U.S. PATENT DOCUMENTS

2004/0053876 A1    3/2004  Turner

FOREIGN PATENT DOCUMENTS

| | | |
|---|---|---|
| DE | 10048417 A1 | 4/2002 |
| EP | 0941318 B1 | 1/2001 |
| WO | WO98/21322 A | 5/1998 |
| WO | WO01/87348 A2 | 11/2001 |
| WO | WO2004/016786 A | 2/2004 |
| WO | WO2004/044135 A | 5/2004 |
| WO | WO2005/116223 A | 12/2005 |

OTHER PUBLICATIONS

Pelletier et al.: "Internal initiation of translation of eukaryotic mRNA directed by a sequence derived from poliovirus RNA", in: Nature, vol. 334, Jul. 1988.
Bormann et al.: "Comparison of picornaviral IRES-driven internal initiation of translation in cultured cells of different origins", in: Nucleic Acids Research, vol. 25, No. 5, 1997.
Dirks et al.: "Dicistronic transcription units for gene expression in ammalian cells", in: Gene, vol. 128, 1993, pp. 247-249.
Espéret et al.: "Non-erythroid genes inserted on either side of human HS-40 impair the activation of its natural α-globin gene targets without being themselves preferentially actvivated", in: The Journal of Biological Chremistry, vol. 275, Aug. 18, 2000, pp. 25831-25839.
Fussenegger et al.: Controlled proliferation by multigene metabolic engineering enhances the productivity of Chinese hamster ovary cells, in: Nature Biotechnology, vol. 16, May 1998.
Jang et al.: "A segment of the 5' nontranslated region of encephalomyocarditis virus RNA directs internal entry of ribosomes during in vitro translation", in: Journal of Virology, vol. 62, No. 8. Aug. 1988, pp. 2636-2643.
Mielke et al.: "Stabilized, long-term expression of heterodimeric proteins from tricistronic mRNA", in: Gene 254, 2000.
Zitvogel et al.: "Construction and characterization of retroviral vectors expressing biologically active human interleukin-12", in: Human Gene Therapy,5, Dec. 1994, pp. 1493-1506.
Tsang et al.: "mammalian Expression vector with two multiple cloning sites for expression of two foreign genes", in: BioTechniques, vol. 22, No. 1, 1997.
Seeman et al.: "DNA nanotechnology: novel DNA constructions", in: Annu. Rev. Biophys. Biomol. Struct., vol. 27, 1998, pp. 225-248.
Seeman: "Nucleic acid junctions and lattices", in: Journal theor. Biol., vol. 99, 1982, pp. 237-247.

*Primary Examiner* — Jon E Angell
(74) *Attorney, Agent, or Firm* — 24IP Law Group; Timothy R DeWitt

(57) ABSTRACT

The invention relates to expression constructs for targeted inhibition of gene expression and methods for their production and which, after transfection thereof into eukaryotic cells, are suitable for inhibiting in a targeted manner these cells formation of defined proteins by RNA interference, wherein the method is a three step method requiring no PCR steps and is carried out in one reaction vessel in a few hours and are suitable for multiple gene expression inhibition.

8 Claims, 6 Drawing Sheets

DNA CONSTRUCTS FOR SPECIFIC INHIBITION OF GENE EXPRESSION BY RNA INTERFERENCE

BACKGROUND OF THE INVENTION

The invention relates to methods for the production of vectors that, after their transfection into eukaryotic cells, are suitable for inhibiting in a targeted manner by means of RNA interference the formation of one or several proteins, and also to such vectors.

One possibility shown recently of inhibiting gene expression is based on the synthesis of double-stranded RNA molecules. Individual genes can be switched off in a targeted manner very effectively and faster using this double-strand RNA (dsRNA) than with any other method, without disrupting the protein formation of neighbouring genes. The underlying principle is termed RNA interference, called RNAi for short. The dsRNA sequence causing this phenomenon is termed siRNA (small interference RNA).

The siRNA does not prevent the gene from being read but switches on a mechanism of the cell, which prevents production of mRNA molecules read off from the gene and thus prevents the formation of the corresponding protein (post-transcriptional gene silencing).

This targeted degradation of mRNA is triggered by short siRNA molecules with a length of 19 to 23 RNA bases, which are homologous to the target mRNA whose transcription into a protein is to be prevented. The siRNA molecules combine with special endoribonucleases to form an RNA protein complex of the cell called "RISC" (RNA-induced silencing complex). As these complexes are built up, the two strands of RNA dissociate, resulting in so-called activated RISCs, which each contain a single strand of the siRNA molecule. Activated RISCs containing the antisense strand that is complementary to the target mRNA bind to the latter and the endoribonuclease of the RNA-protein complex now ensures the sequence-specific degradation of the mRNA.

The siRNA can be created in the cell experimentally or it can be transported in from the outside. This is done using synthetically produced siRNA molecules, which can be administered both in vitro and in vivo.

However, this method has technical limits. Alongside the general instability of the synthetic siRNA in the medium and also in the cell, inhibition using synthetic siRNA is in principle possible only temporarily, and many cells (e.g. neuronal cells) can be transfected only very inefficiently. Studies based on the transfection of synthetic siRNA are therefore limited as a rule both in terms of time, to 1 to 5 days, and in terms of cell type. Furthermore, the high production costs and the lengthy production also represent disadvantages.

The other method is to create siRNA in the cell by means of vectors. These are viral or plasmid-based vectors that only lead to the formation of the siRNA sequences by means of expression once they are in the cell. The advantages compared to transfection with synthetic siRNA are the more stable and more regulated transcription of the corresponding siRNA sequence.

However, the plasmid-based vectors not only exhibit a low transfection efficiency but also have an elaborate production process. It is therefore necessary to select stable clones. This process is often lengthy and can take weeks or even months, with the frequent occurrence of numerous potential difficulties that are inherent to the cloning experiments. For checking the product, sequencing procedures are necessary that are also labour-intensive and costly.

Furthermore, plasmid-based vectors contain antibiotic-resistance genes, which are necessary for their selection. For this reason, such vectors are not suitable for application in living organisms. The possible recombination with ubiquitous bacteria occurring in the organism harbours the risk of increasing occurrence of bacteria resistant to antibiotics. The spread of resistance to antibiotics is a serious problem and such a path would be irresponsible.

As viral vectors are capable of efficient and targeted transfection, they offer an advantage compared to synthetic siRNA molecules and to plasmid-based vectors.

However, there are reservations restricting the use of such viral vectors in therapeutic application. Here, too, the recombination of viral sequences with naturally occurring viruses represents an inherent safety risk, since the creation of new, pathogenic hybrid viruses must be feared. In addition, their production is elaborate and costly.

As even the inhibition of the expression of only one gene product with the use of expression systems is associated with a large number of complications, it is almost axiomatic that simultaneously switching off the expression of several gene products in a cell or a tissue is much more complex and therefore more difficult to accomplish.

One of the main problems with the multiple inhibition of gene expression by RNA interference, when several independent constructs are used, is the low probability that a cell will be transfected by only one construct. This low probability decreases exponentially with the number of constructs used. Often, however, for certain approaches in genetic therapy a controlled, simultaneous inhibition of gene expression is required.

A large number of methods exist that enable the cotranscription of several RNA molecules in a cell. The simplest method is the cotransfection of two independent expression constructs (in the following also called vectors). Another method consists of transfection with a vector carrying the two independent expression cassettes. Such constructs can also be used for the synthesis of siRNA molecules.

With both possibilities there is however the danger that the transcripts differ significantly in relation to their number, processing, half-lives and translational efficiency and therefore in the quantity of the protein expressed, with the result that their use is characterised by ineffectiveness and poor reproducibility. Therefore the use of such expression systems would also lead to siRNA transcription of varying degrees, which would ultimately result in the unequal inhibition of the relevant genes.

The construction of dicistronic and polycistronic RNA molecules with the use of IRES (internal ribosome entry site) elements represents another possibility for the coexpression of several genes. The latter allow the initiation of the translation by ribosomes independently of the mRNA cap structure by sequence elements. For the first time IRES elements have been discovered in the mRNA of the picornavirus (Pelletier and Sonenberg, 1988, Nature 334: 320-325, Jang et al., 1988, Journal Virology 62: 2636-2643).

For the construction of bicistronic vectors, most frequently the IRES elements of the poliovirus and EMCV (encephalomyocarditis virus) are used (Dirks et al., 1993, Gene 128: 247-249). Unfortunately their efficiency varies strongly depending on the cell line used (Borman et al., 1997, Nucleic Acids Res. 25: 925-932).

Most of the available bicistronic expression cassettes consist of a selectable marker or a reporter gene, which are arranged on the 3'-side of the IRES element and an MCS (multiple cloning site) for the insertion of the desired gene (Dirks et al., 1993, Gene 128: 247-249). Tricistronic and polycistronic expression systems with the use of IRES elements are also known (Zitvogel et al., 1994, Hum Gene Ther 5: 1493-1506, Fussenegger et al., 1998a, Nature Biotechnol. 16: 468-472, Mielke et al., 2000, Gene 254. 1-8).

However, there are reservations restricting the use of viral IRES elements in therapeutic application. Here, too, the recombination of viral sequences with naturally occurring viruses represents an inherent safety risk, since the creation of new, pathogenic hybrid viruses must be feared.

Multicistronic vectors can also be constructed by linking transcription units without IRES elements. On the one hand, the desired genes can be cloned via various MCS into a plasmid vector, and on the other, expression cassettes isolated from plasmids can be connected by DNA linkers to form linear multicistronic vectors (sang et al., 1997, Bio Techniques 22: 68).

However, investigations of the expression rates of linear cis-linked genes have shown a strong negative influence on the transcription of expression cassettes arranged in this manner (Esperet et al., 2000, J Biol Chem 275: 25831-25839).

Plasmid vectors for the expression of multiple genes differ from the conventional plasmid vectors in the number of cloned transcription units. In this context promoters or poly(A) sequences of identical or different origin can be used for the transcription units.

The disadvantage that arises from the use of differing promoters is that the promoters differ in their strength and therefore the expression rates of the individual genes can vary, yet the use of identical promoters can lead to formation of secondary DNA structures, which can lead to loss of function of the promoters as a consequence.

All the mentioned vectors for multiple gene expression have in common that they are based either on plasmids or on viral vectors. Alongside all the shortcomings described of the current multiple-coding vectors, in addition they exhibit the disadvantages of this type of vector. The disadvantages of viral vectors, which include instability of the attenuated vaccination strain, and the shortcomings of plasmid DNA vectors, such as the spread of resistance genes against antibiotics that accompanies their use (described in detail in EP 0 941 318 B1), are sufficiently well known.

Therefore it would be desirable to have expression systems for siRNA that are also in a position to inhibit the gene expression of several genes simultaneously. Probably the greatest problem in resolving this question is a linker connecting the sequences to create the siRNA molecules, which in each case ensures sufficient transcription for inhibition of gene expression of these sequences.

SUMMARY OF THE INVENTION

One method for linking DNA fragments using DNA connecting elements is known from the literature. Seeman describes DNA sequences for investigating naturally occurring branched junctions, called Holliday junctions, which are postulated as special topological forms of B-DNA under torsional stress (Seeman: 1982, J Theor Biol 99: 237-247; Annu. Rev. Biophys. Biomol. Struct. 1998. 27: 225-248). To date the application of these structures has remained limited to short oligonucleotide pieces for the investigation of forms of DNA structure.

A polyfunctional connection is known from DE 100 48 417 A1, which describes the conjugation of two reactive functional groups by means of a linker. Nucleic acids are also mentioned as biological substances that can also be coupled in this manner; however the examples show only the applications of the invention for the conjugation of peptides. WO 01/87348 A2 describes another approach for trans-porting several genes into cells for efficient expression. Nucleic acids are to be linked by covalent bonds to form supramolecular structures called dendrimers.

One further possibility for producing vectors for siRNA is shown by http://www.ambion.com. This process avoids the above-mentioned disadvantages. However, this production process too is time-consuming and very susceptible to errors due to a number of necessary multiplication steps for the relevant sequences by means of a PCR (polymerase chain reaction). There is a very great possibility of producing both undesired and unnoticed mutations, which are amplified by the PCR process. So here, too, control sequencing measures are necessary which prolong the production process and contribute to increased costs.

In view of this state of the art, it is the task of the invention to provide a suitable method for in vitro or in vivo synthesis of one or several defined siRNA sequences, the expression constructs thus produced and a kit for carrying out the synthesis.

This task is fulfilled by the features of the independent claims.

Therefore according to the invention an expression construct is envisaged that comprises a first terminal DNA hairpin loop, in which a single strand of deoxyribonucleotides is folded back on itself to form a double-stranded region so that the latter exhibits one end with a cohesive overhang and at the opposite end the individual strands forming the double strand are connected to each other by a single-stranded loop, a second terminal hairpin loop, which is constructed analogously to the first terminal hairpin loop, and a T-shaped DNA structure with three double-stranded DNA arms that are connected via Holliday junctions, whereby at least one arm contains the sequences to be transcribed, and at the end that is opposite to the connection with the other arms the individual strands of this double-stranded DNA arm are connected to each other by a single-stranded DNA loop, and the two other arms exhibit cohesive ends, whereby one arm exhibits a suitable termination sequence and the other arm a suitable promoter sequence.

The components mentioned are the essential parts of a construct according to the invention. The invention also comprises expression constructs with these components whereby, however, the latter arise from other combinations of DNA structures.

Furthermore according to the invention an expression construct is envisaged for the targeted inhibition of gene expression by means of RNA interference, which exhibits a first terminal DNA hairpin loop, in which a single strand of deoxyribonucleotides is folded back on itself to form a double-stranded region so that the latter exhibits one end with a cohesive overhang and at the opposite end the individual strands forming the double strand are connected to each other by a single-stranded loop and, further, a second terminal hairpin-shaped loop, which is constructed analogously to the first terminal hairpin loop and whose double-stranded and single-stranded regions consist of the sequence to be transcribed and a suitable promoter sequence and a suitable reverse-complementary termination sequence, which are located between the two terminal hairpin loops described above in a double strand of DNA.

Such an expression construct exhibits only one double-stranded copy of the siRNA to be synthesised. The production of an siRNA in the presence of only one copy is possible with this construct, since the sequences to be transcribed are read off and transcribed by the RNA polymerase even beyond the single-stranded loop. This would not be possible with a double-stranded plasmid.

For both expression constructs according to the invention it is envisaged that several T-shaped or linear DNA structures are connected in each case at an end by a linker by means of Holliday junctions. In this case it is envisaged that the sequences to be transcribed encode identical or different genes.

Linkers are to be understood as oligonucleotides for connecting DNA expression cassettes. A linker according to the invention consists of two or more strands, as illustrated by the following example of a linker, formed from three oligonucleotides that are linked with three expression cassettes to strands A, B and C that are connected to one another: the 5'-end of A has a sequence complementary to the 3'-end of B and forms a double strand, while the 3'-end of A pairs with the 5'-end of C, and finally the 5'-end of B pairs with the 3'-end of C. This type of connection of DNA double strands is also termed a Holliday junction (F. W. Stahl: Genetics. 1994 October; 138(2): 241-6), which has the advantage that solely naturally occurring components are used for linking the expression cassettes, which can prove to be especially advantageous when the invention is used for medical purposes, for toxicological reasons.

The oligodeoxynucleotide sequences used for the branching DNA junctions are selected such that with hybridisation at the 5'-ends of the oligonucleotides (for example) in each case one overhanging cohesive end is created that is four bases long. The sequences of the cohesive ends can differ for each arm of a junction, but they do not have to. The T-shaped or linear DNA structures exhibit an overhang that is complementary to the cohesive end. This enables targeted ligation of the expression cassettes to the individual "arms" of the junctions.

Such expression constructs according to the invention are suitable for targeted, multiple inhibition of gene expression of various genes. Owing to the identical construction of the T-shaped structures that contain the sequences necessary in each case for producing the siRNA molecules, the different siRNA molecules are synthesised in equal quantities. The number of genes whose protein expression is inhibited depends on the number of T-shaped structures connected via the linker.

It is an advantage that in an alternative embodiment of the expression construct according to the invention the cohesive ends of individual components are selected to be specific and distinct from one another for targeted connections with other components. This allows the targeted construction of the desired expression construct.

A DNA expression construct that contains the sequences for synthesising one or more siRNA molecules can transfect cells in a targeted manner.

Transfection is to be understood as the introduction of nucleic acid sequences into the cell using biological, chemical or physical methods, the consequence of which is lasting or temporary expression of catalytic RNA transcripts encoded by these sequences in the transfected cell.

In a further development the expression constructs according to the invention exhibit one or several covalently linked peptides, proteins, carbohydrates, antibodies or steroids.

The invention also relates to production methods for expression constructs that after their transfection into eukaryotic cells inhibit the formation of defined proteins in a targeted manner by means of RNA interference.

A method is envisaged for linear expression constructs, beginning in method step a) with the mixing of a DNA double strand, which contains a singular copy, 19 to 23 bases long, of a gene sequence or its reverse-complementary sequence and a termination signal for RNA polymerases and is closed at one end by a sequence loop that is 8 to 12 bases long, which is selected such that opposite bases are never complementary to one another and the flanking DNA single strands are connected together to form a DNA double strand, which exhibits at the other end a short protruding DNA single strand, with a hairpin-shaped oligodeoxynucleotide, which exhibits at its end short protruding ends of single-stranded DNA, in method step b) and in method step c) a promoter with short protruding ends of single-stranded DNA, whereby the single-stranded 5'-end of the promoter can pair with the hairpin-shaped oligodeoxynucleotide or the 10 to 1000 base long double strand and the single-stranded 3'-end of the promoter is complementary to the single-stranded 5'-end of the DNA double strand described under a), with following ligation of the DNA fragments in method step d) and final purification of the vectors synthesised, in the last method step e).

The method according to the invention may optionally be designed for the synthesis of linear expression constructs such that before addition of the hairpin-shaped oligodeoxynucleotide in method step c) a 10 to 1000 (=n) base long DNA double strand of a non-coding sequence with short protruding ends of single-stranded DNA is added, whereby the single-stranded 3'-end can pair with the single-stranded 5'-end of the promoter and the single-stranded 5'-end is complementary to the single-stranded 3'-end of the hairpin-shaped oligodeoxynucleotide.

For the synthesis of T-shaped expression constructs that after their transfection into eukaryotic cells inhibit the formation of defined proteins in a targeted manner by means of RNA interference, a method is envisaged beginning in method step a) with the mixing of a T-shaped DNA double strand, which contains a singular copy, 19 to 23 bases long, of a gene sequence in the 5' to 3' direction and a termination signal for RNA polymerases and is closed at one end by a 8 to 12 base long sequence loop, which is selected such that opposite bases are never complementary to one another and the flanking double-strand regions are thus linked with one another by two DNA single strands, and at the other end exhibits two short protruding DNA single strands, and an oligodeoxynucleotide whose sequence is complementary to the two short protruding DNA single strands and forms two short protruding ends of single-stranded DNA, in method step b) with a hairpin-shaped oligodeoxynucleotide, which at its end exhibits short protruding ends of single-stranded DNA and in method step c) a further hairpin-shaped oligodeoxynucleotide, which at its end exhibits short protruding ends of single-stranded DNA complementary to the T-shaped DNA double strand from a) and in method step d) a promoter with short protruding ends of single-stranded DNA, whereby the single-stranded 5'-end of the promoter can pair with the hairpin-shaped oligodeoxynucleotide from b) and the single-stranded 3'-end of the promoter is complementary to the single-stranded 5'-end of the T-shaped DNA double strand, followed by ligation of the DNA fragments in method step e), whereby the construct can also be synthesised without the 10 to 1000 base long DNA double strand, and final purification of the synthesised vectors in the final method step f).

According to the invention this production method includes after method step c) the addition of a 10 to 1000 base (=n) long DNA double strand of a non-coding sequence with short protruding ends of single-stranded DNA, whereby the single-stranded 3'-end can pair with the single-stranded 5'-end of the promoter and the single-stranded 5'-end complementary to the single-stranded 3'-end of the hairpin-shaped oligodeoxynucleotide from method step b) is added and/or the addition of a 10 to 1000 base (=n) long DNA double strand of a non-coding sequence with short protruding ends of single-stranded DNA, whereby the single-stranded 5'-end can pair with the single-stranded 3'-end of the T-shaped DNA double strand and the single-stranded 3'-end is complementary to the single-stranded 5'-end of the hairpin-shaped oligodeoxynucleotide from method step c).

In a preferred embodiment a method is envisaged in which the promoter is part of a bacterially amplifiable plasmid, which is excised before the mixing of the components using a restriction endonuclease that recognises an interface flanking the promoter on the plasmid, an interface that is not present on the molecule to be synthesised.

In principle the promoters envisaged may be any promoters that are operable in the target cells, that is in the cells in which the gene expression is to be inhibited. These promoters are preferably of human origin, if human cells or tissues are transfected with the expression constructs according to the invention. However they can also, for example, be of viral, bacterial or parasitic origin or from species other than the target species. The promoters envisaged are in particular, but not restricted to, the human U6 promoter, the human H1 promoter, the murine U6 promoter, the CMV promoter and the 7SK promoter.

Furthermore, it is envisaged according to the invention that if a promoter is used as part of a bacterially amplifiable plasmid, the ligation step takes place in the presence of the restriction endonuclease with which the promoter was excised from the plasmid.

In one embodiment, digestion of the reaction mixture is carried out before the final purification step, using an exonuclease that is exclusively specific for 3' DNA ends or 5' DNA ends.

In the method according to the invention the DNA double strand that is added at the beginning of the mixing may result from the annealing of a partially self-complementary oligodeoxynucleotide or from two complementary oligodeoxynucleotides. The annealing may also take place in the reaction mixture itself, so at the beginning of the method according to the invention only single-stranded complementary oligodeoxynucleotides are added.

In a preferred embodiment the sequence of the oligodeoxynucleotides is selected such that the resulting hairpins exhibit in their double-stranded region the recognition sequence for a restriction endonuclease.

The final purification of the vectors synthesised using the method according to the invention takes place preferably by means of either chromatography or gel electrophoresis.

If the promoter is used in the production method according to the invention as part of a bacterially amplifiable plasmid, the restriction endonuclease with which the promoter can be excised from the plasmid is an enzyme of the group of class II restriction endonucleases, preferably from the group BbsI, BbvI, BbvII, BpiI; BpII, BsaI, BsmI, BsmBI, BsmFI, BspMI, Eam1104I, EarI, Eco31I, Esp3I, FokI, HgaI, SfaNI or their isoschizomers.

The invention also relates to a kit for carrying out the method according to the invention, containing at least one promoter, hairpin-shaped oligodeoxynucleotides and enzymes. The enzymes are ligases, restriction endonucleases, restriction exonucleases, kinases and polymerases or selected combinations thereof in the form of an enzyme mix. In addition, depending on the embodiment the kit may also contain means for carrying out the enzymatic reactions and means for purification of the vectors produced. The promoter may be contained in the kit as part of a plasmid from which it can be excised using a suitable restriction endonuclease.

Furthermore a kit is envisaged that allows the synthesis of the multiple RNAi expression constructs, which contain the T-shaped structure described. In addition to the components already mentioned, the kit also contains a T-shaped structure into whose double-stranded arm with the sequence to be transcribed the desired sequence can be inserted.

If a linker with Holliday junctions is used, the expression constructs according to the invention for targeted inhibition of gene expression by means of RNA interference are suitable for inhibiting the expression of more than one gene. Owing to the special structure of the constructs according to the invention, the sequences to be transcribed for forming the siRNA are read off to the same extent by the RNA polymerase.

The number of genes that are inhibited after transfection of a multiple inhibition construct according to the invention depends on the number of double-stranded arms that the linker exhibits.

In relation to the invention neither the cotransfection of two separate vectors, nor the method described in DE 100 48 417 A1 for chemically linking the coding gene sequences with the necessary control elements (promoter, poly(A) signal), is a close prior art. In cotransfection using lipofection, different vectors are also indeed brought into physical proximity with one another and transported into the cell, but the underlying principle of this method is different. Moreover, unfortunately the chemical conjugation described of expression constructs leads to structures with a much greater molecular weight, which are known to be more difficult to transport into cells. The same also applies to the method described in WO 01/87348 A2 for constructing a dendrimer containing nucleic acids. In addition, the method described for constructing dendrimers is an elaborate production process consisting of several stages.

The invention also relates to a drug, preferably a vaccine, which contains one of the expression constructs according to the invention. Such drugs can be applied in humans and animals locally and systemically, and are suitable for the treatment of infections, for example infections with herpes viruses, papilloma viruses and lentiviruses, for the treatment of metabolic disorders, such as for example Parkinson's disease and cystic fibrosis, for the treatment of cardiovascular diseases, for the treatment of cancers, such as for example carcinomas, melanomas and sarcomas, for the treatment of additional diseases, such as for example age-related macula degeneration, and for treatment after inflammations, injuries or surgical procedures, which for example can affect the spinal cord, the brain and other organs.

Further advantageous measures are described in the other dependent claims; the invention is described in more detail using examples of embodiments and the following Figures; they show the following:

DETAILED DESCRIPTION OF PREFERRED EMBODIMENTS

Figure 1:
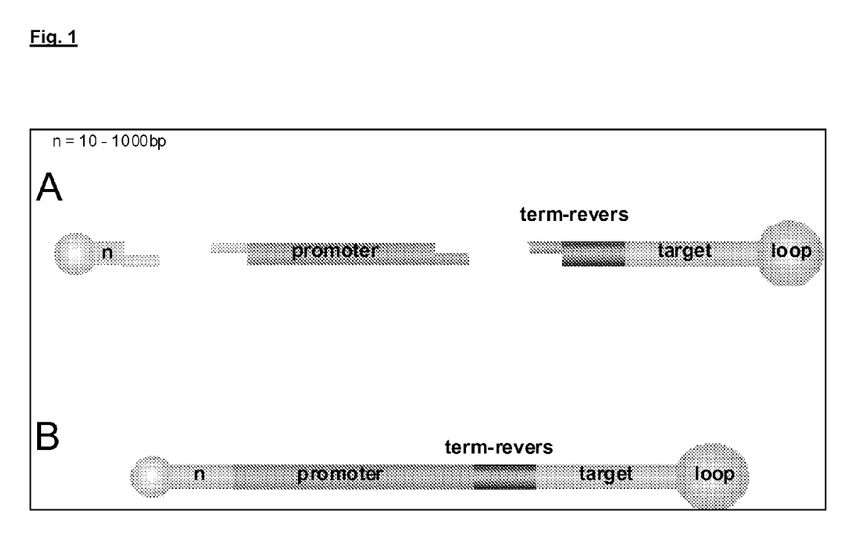
FIG. 1 Components of the linear siRNA vectors

FIG. 1: shows the components of the linear siRNA vectors

A: SiRNA sequence to be used in the method, homologous to the target mRNA. The sequence consists of a sense or antisense region (target), a sequence loop 8 to 12 bases long, and a reverse complementary termination sequence. The siRNA sequence may consist of individual ODN fragments, which must be annealed, ligated and if applicable phosphorylated with the aid of the enzyme mix; it may also already be present as a complete ODN fragment.

Further, the components that are ligated to the ODN fragment by the enzyme ligase. These components are the promoter sequence with corresponding complementary overhangs and a hairpin-shaped oligodinucleotide whose own complementary and unique overhang of four bases in each case leads to a covalently closed linear vector arising, which consists of promoter, target sequence and termination sequence and which has closed hairpin-shaped ends.

Between the promoter and the terminal oligonucleotide, a 10 to 1000 base (=n) long DNA double strand of a non-coding sequence with short protruding ends of single-stranded DNA may be used.

B: Final product ready for transfection

Figure 2:
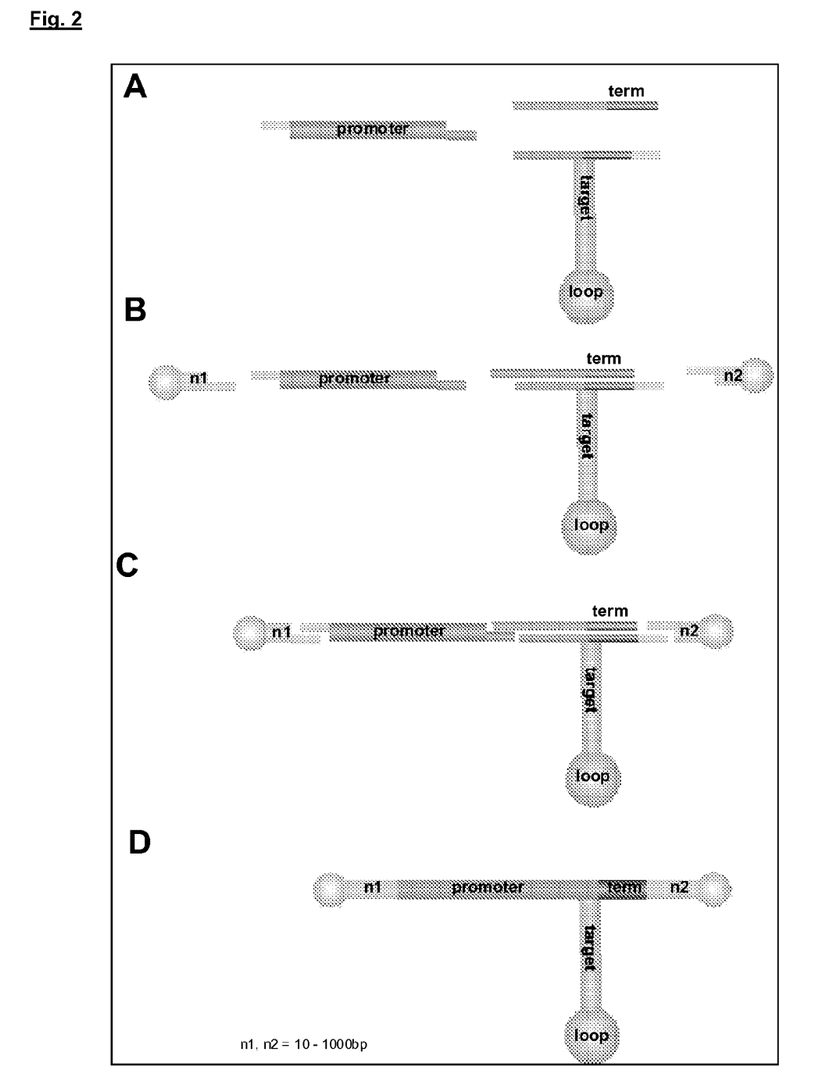
FIG. 2 Components of the T-shaped siRNA vectors

FIG. 2: shows the components of the T-shaped siRNA vectors

A: SiRNA sequence to be used in the method, homologous to the target mRNA. The sequence consists of a sense or antisense region (target), a sequence loop 8 to 12 bases long, and a termination sequence. The siRNA sequence may consist of individual ODN fragments, which must be annealed, ligated and if applicable phosphorylated with the aid of the enzyme mix; it may also already be present as a complete ODN fragment.

B/C: Further, the components that are ligated to the ODN fragment by the enzyme ligase. These components are the promoter sequence with corresponding complementary overhangs and hairpin-shaped oligodinucleotides whose own complementary and unique overhangs of four bases in each case lead to a covalently closed vector arising, which consists of promoter, sense loop or antisense loop and termination sequence and which has closed hairpin-shaped ends.

Between the promoter and the terminal oligonucleotide, and between the termination sequence and the terminal oligonucleotide, a 10 to 1000 base (=n) long DNA double strand of a non-coding sequence with short protruding ends of single-stranded DNA may be used.

D: Final product ready for transfection

Figure 3:
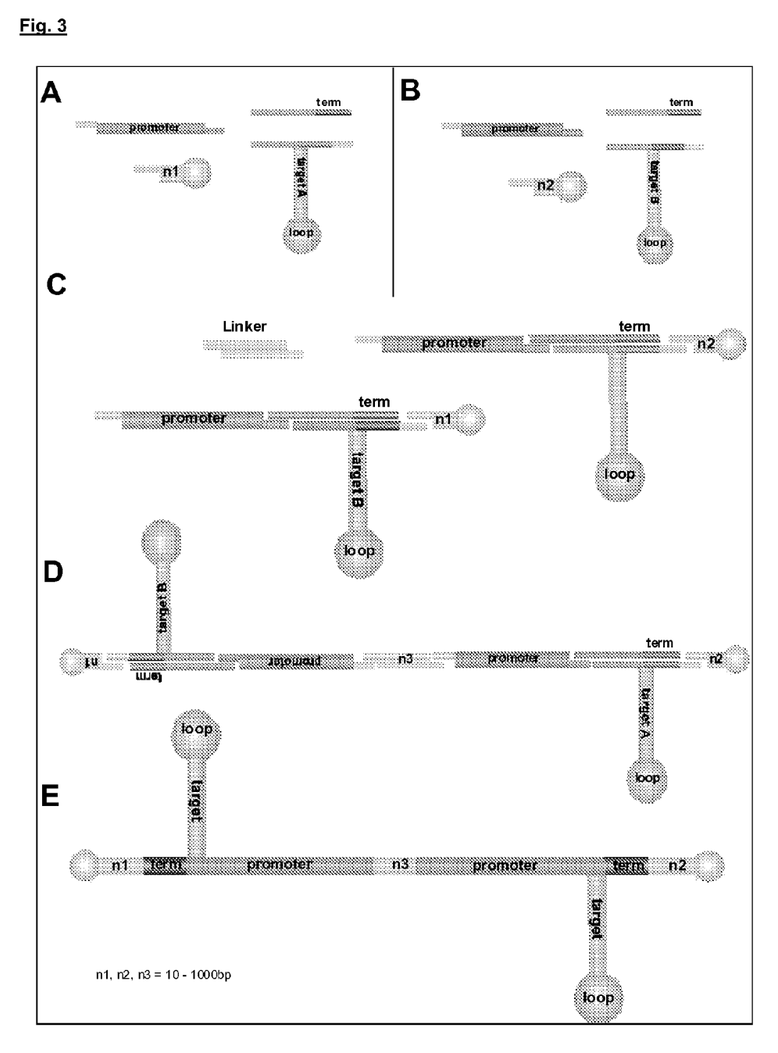
FIG. 3 Components of the T-shaped double siRNA vectors

FIG. 3: shows the components of the T-shaped multi-siRNA vectors (di-construct)

A/B/C/D: SiRNA sequences to be used in the method, homologous to the target mRNA. The two sequences consist of a sense or antisense region (target A, target B), a sequence loop 8 to 12 bases long, and a termination sequence. The siRNA sequences may consist of individual ODN fragments, which must be annealed, ligated and if applicable phosphorylated with the aid of the enzyme mix; they may also already be present as a complete ODN fragment. Further, the components that are ligated to the ODN fragment by the enzyme ligase. These components are the promoter sequence with corresponding complementary overhangs, a DNA double strand linker, and hairpin-shaped oligodinucleotides, whose own complementary and unique overhangs of four bases in each case lead to a covalently closed vector arising, which consists of promoter, sense loop or antisense loop and termination sequence and which has closed hairpin-shaped ends.

Between the promoter and the terminal oligonucleotide, between the termination sequence and the terminal oligonucleotide, and in each case between the linker and the promoter, a 10 to 1000 base (=n) long DNA double strand of a non-coding sequence with short protruding ends of single-stranded DNA may be used.

E: Final product ready for transfection

Figure 4:
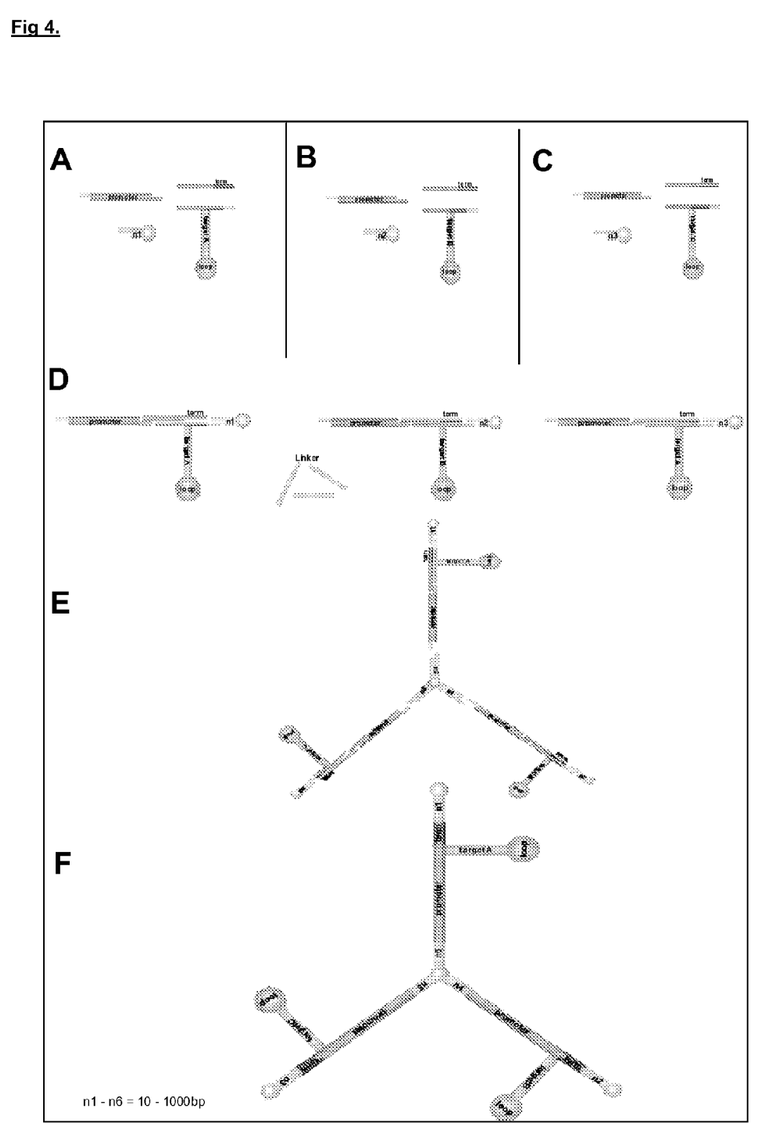
FIG. 4 Components of the T-shaped triple siRNA vectors

FIG. 4: shows the components of the T-shaped multi-siRNA vectors (tri-construct)

A/B/C/D/E: SiRNA sequences to be used in the method, homologous to the target mRNA. The three sequences consist of a sense or antisense region (target A, target B), a sequence loop 8 to 12 bases long, and a termination sequence. The siRNA sequences may consist of individual ODN fragments, which must be annealed, ligated and if applicable phosphorylated with the aid of the enzyme mix; they may also already be present as a complete ODN fragment. Further, the components that are ligated to the ODN fragment by the enzyme ligase. These components are the promoter sequence with corresponding complementary overhangs, a DNA double strand linker and hairpin-shaped oligodinucleotides, whose own complementary and unique overhangs of four bases in each case lead to a covalently closed vector arising, which consists of promoter, sense loop or antisense loop and termination sequence and which has closed hairpin-shaped ends.

Between the promoter and the terminal oligonucleotide, between the termination sequence and the terminal oligonucleotide, and in each case between the linker and the promoter, a 10 to 1000 base (=n) long DNA double strand of a non-coding sequence with short protruding ends of single-stranded DNA may be used.

F: Final product ready for transfection

Figure 5:
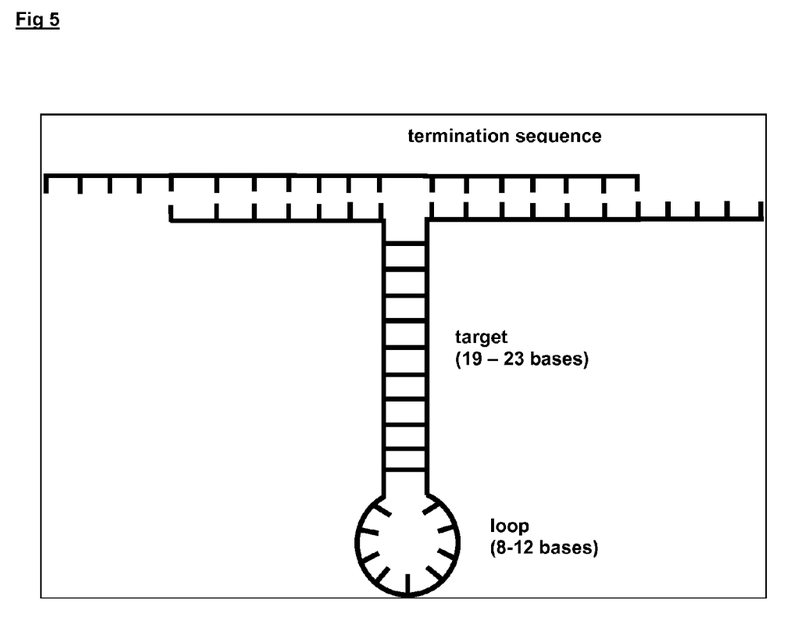
FIG. 5 Detailed representation of the target sequence loop of the T-shaped constructs FIGS. 6/7 Experimental results of the comparison of T-shaped siRNA expression vector (T-siRNA-CDC2) according to the invention with synthetic RNA (CDC2-RNA), which contains the identical target sequences.

FIG. 5: shows a detailed representation of the target sequence loop of the T-shaped constructs.

Figure 6:
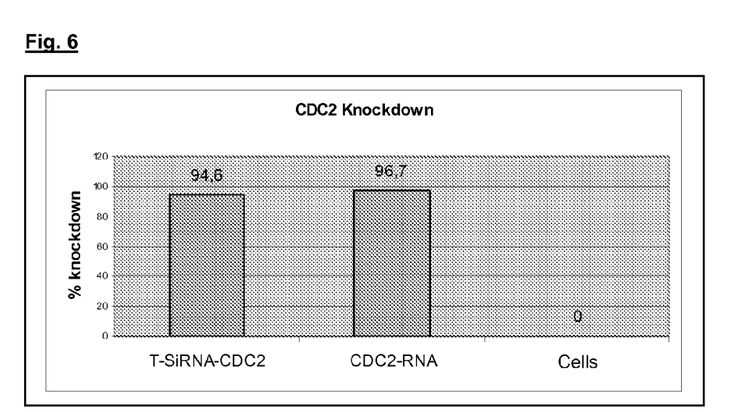

FIG. 6: shows the results of an experiment in which the T-shaped siRNA expression vector (T-siRNA-CDC2) according to the invention is compared with synthetic RNA (CDC2-RNA) that contains the identical target sequences.

CDC2 mRNA was determined using quantitative real-time PCR after transfection of HeLa cells. The following were used: T-shaped siRNA vector produced using the method according to the invention, which contains a CDC2 target sequence; synthetic RNA of the same CDC2 target sequence; and untreated cells. The values represent mean values that were calculated from multiple determinations. With the untreated cells suppression of the CDC2 mRNA was not observed, as expected. By contrast, the cells treated with the T-shaped siRNA vector and the synthetic RNA demonstrated a significantly smaller quantity of CDC2 mRNA. This is reduced by up to 96.7% in comparison to the positive control (untreated cells).

Figure 7:
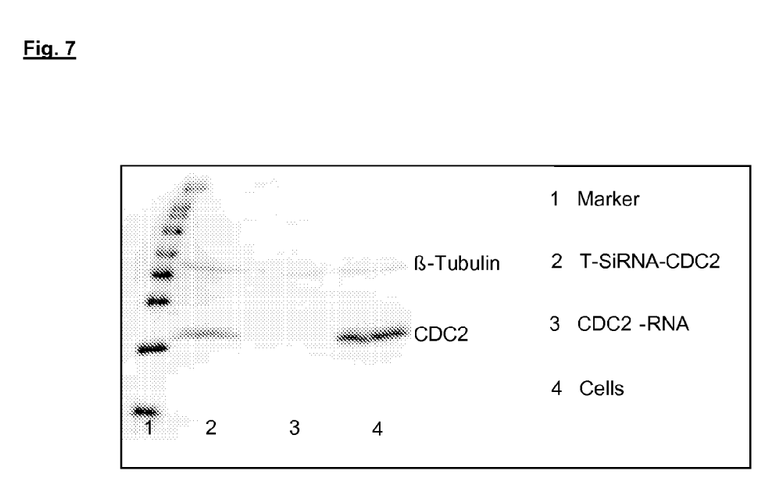

FIG. 7: shows the results of an experiment in which the T-shaped siRNA expression vector (T-siRNA-CDC2) according to the invention is compared with synthetic RNA (CDC2-RNA) that contains the identical target sequences.

CDC2 protein was determined by a Western blot after transfection of HeLa cells. The following were used: T-shaped siRNA vector produced using the method according to the invention, which contains a CDC2 target sequence; synthetic RNA of the same CDC2 target sequence; and untreated cells. β-tubulin was used as an internal standard. With the untreated cells (band 4) the suppression of the CDC2 mRNA was not observed, as expected. By contrast, the cells treated with the T-shaped siRNA construct (band 2) and the synthetic RNA (band 3) demonstrated a significantly smaller quantity of CDC2 protein.

The suppression of gene expression by the T-shaped siRNA constructs that were produced with an "siRNA expression vector kit" using the method according to the invention is comparable with the effects of synthetic RNA transfections. The suppression of gene expression is in the region between 94 and 96% in both transfections.

EXAMPLE 1

Production of T-Shaped siRNA Vector for Suppressing CDC2 Expression

The vector coding for the siRNA of the CDC2 was obtained as follows:
The two ODN fragments for CDC2 were heated for 3 min at 90° C. and annealed by slow cooling. In this manner the following sequence coding for CDC2 was obtained:

```
Seq. ID 1:      TGGGGTCAGCTCGTTACTCTCTC
```

Here the 19 bases form the sense strand, while the following four bases (underlined) form the beginning of the loop sequence.
Phosphorylation by PN kinase then followed. To obtain 10 micrograms of end product, 3.9 micrograms of CDC2 were used. Following addition of 5.2 micrograms of H1 promoters (seq. ID 2) and the 5'-phosphorylated hairpin-shaped oligodeoxynucleotides (seq. ID 3 and 4):

```
Seq. ID 2:
ATATTTGCAT GTCGCTATGT GTTCTGGGAAATCACCATAA

ACGTGAAATG TCTTTGGATT TGGGAATCTTATAAGTTCTGT

ATGAGAGCAC AGATAGGG

Seq. ID 3:
5'-PH-GGG AAA GCT TAG TTT TCT AAG CTT-3'

(1.3 micrograms)
and

Seq. ID 4:
5'-PH-GTT GGA ATT CAG TTT TCT GAA TTC-3'

(1.3 micrograms),
``` the individual fragments were ligated with the aid of the enzyme T4 DNA ligase. The resulting mixture of nucleic acids was treated with the enzyme T7 DNA polymerase. The final product, the vector expressing siRNALuc, was purified by column chromatography and was ready for transfection.

What is claimed is:

1. A DNA expression construct for the targeted inhibition of gene expression by means of RNA interference, consisting of the following components:
   a) a first terminal DNA hairpin loop, in which one single strand of deoxyribonucleotides is folded back on itself to form a double-stranded region with a cohesive overhang at one end and a single-stranded loop at the opposite end,
   b) a second terminal hairpin loop having the same construction as the first terminal DNA hairpin loop,
   c) at least one T-shaped DNA structure with three double-stranded DNA arms that are linked via Holliday junctions to each other whereby
      i. one arm contains the sequences to be transcribed comprising a sequence that encodes an RNA that inhibits expression of a target gene by means of RNA interference, and the individual strands of this DNA double-stranded arm are linked to one another at the end that is opposite to the junction with the other arms by a single-stranded DNA loop, and
      ii. the two other arms exhibit cohesive ends, whereby one arm exhibits a suitable termination sequence and the other arm a suitable promoter sequence, and
      iii. wherein each arm only contains one of the following: sequences to be transcribed, a suitable termination sequence or a suitable promoter sequence.

2. The DNA expression construct according to claim 1, wherein relative to i and ii several T-shaped DNA structures are connected at one end by a linker via Holliday junctions.

3. The DNA expression construct according to claim 1, wherein the cohesive ends of each of the components are linkage-specific for a targeted linkage with one or more of the cohesive ends of other components.

4. The DNA expression construct according to claim 1 for targeted inhibition of expression of one or several genes, wherein the sequences to be transcribed code for identical or different genes.

5. The DNA expression construct according to claim 1 for targeted inhibition of expression of one or several genes wherein a protection against exonuclease degradation is achieved by means of a short single-stranded region of three to eight deoxynucleotides, which links the two strands of the linear double-stranded region to each other covalently.

6. The DNA expression construct according to claim 1 for targeted inhibition of expression of one or several genes, wherein the one or several genes are attached covalently in the short single-stranded region to one or several peptides, proteins, carbohydrates, antibodies or steroids.

7. A method for the synthesis of vectors that after their transfection into eukaryotic cells inhibit in a targeted manner the formation of defined proteins by means of RNA interference, comprising the following method steps:
   a) mixing a T-shaped DNA double strand that contains a 19 to 23 base long, singular copy of a gene sequence in the 5' to 3' direction comprising a sequence that encodes an RNA that inhibits expression of a target gene by means of RNA interference, and a termination signal for RNA polymerases located on a different arm of the T-shaped DNA double strand than the gene sequence, and is closed at one end by an 8 to 12 base long sequence loop, which is selected such that opposite bases are never complementary to one another and having flanking double-stranded regions linked with each other by two DNA single strands, and at the other end exhibits two short protruding DNA single strands, and an oligodeoxynucleotide whose sequence is complementary to the two short protruding DNA single strands and forms two short protruding ends of single-stranded DNA, with
   b) a hairpin-shaped oligodeoxynucleotide, which exhibits at its end short protruding ends of single-stranded DNA, and
   c) a further hairpin-shaped oligodeoxynucleotide, which exhibits at its end short protruding ends of single-stranded DNA complementary to the T-shaped DNA double strand from a), and
   d) a promoter with short protruding ends of single-stranded DNA, whereby the single-stranded 5'-end of the promoter can pair with the hairpin-shaped oligodeoxynucleotide from b) and the single-stranded 3'-end of the promoter is complementary to the single-stranded 5'-end of the T-shaped DNA double strand, and
   e) then ligating the DNA fragments, and
   f) final purification of the vectors synthesised.

8. The method for synthesis according to claim 7, wherein after method step c) a 10 to 1000 base long DNA double strand of a non-coding sequence with short protruding ends of single-stranded DNA is added, whereby the single-stranded 3'-end can pair with the single-stranded 5'-end of the promoter and the single-stranded 5'-end is complementary to the single-stranded 3'-end of the hairpin-shaped oligodeoxynucleotide from method step b) and/or a 10 to 1000 base long DNA double strand of a non-coding sequence with short protruding ends of single-stranded DNA is added, whereby the single-stranded 5'-end can pair with the single-stranded 3'-end of the T-shaped DNA double.strand and the single-stranded 3'-end is complementary to the single-stranded 5'-end of the hairpin-shaped oligodeoxynucleotide from method step c).

* * * * *

SEQUENCE LISTING

```
<160> NUMBER OF SEQ ID NOS: 4

<210> SEQ ID NO 1
<211> LENGTH: 23
<212> TYPE: DNA
<213> ORGANISM: Artificial
<220> FEATURE:
<223> OTHER INFORMATION: synthetic deoxyoligonucleotide
<220> FEATURE:
<221> NAME/KEY: misc_feature
<223> OTHER INFORMATION: first 19 bases are sense CDC2, last 4 bases are
      beginning of loop

<400> SEQUENCE: 1
tggggtcagc tcgttactct ctc                                          23

<210> SEQ ID NO 2
<211> LENGTH: 99
<212> TYPE: DNA
<213> ORGANISM: Homo sapiens
<220> FEATURE:
<221> NAME/KEY: misc_feature
<223> OTHER INFORMATION: Promotor of Human Gene for H1 RNA

<400> SEQUENCE: 2
atatttgcat gtcgctatgt gttctgggaa atcaccataa acgtgaaatg tctttggatt    60
tgggaatctt ataagttctg tatgagagca cagatagg                           99

<210> SEQ ID NO 3
<211> LENGTH: 24
<212> TYPE: DNA
<213> ORGANISM: Artificial
<220> FEATURE:
<223> OTHER INFORMATION: synthetic deoxyoligonucleotide
<220> FEATURE:
<221> NAME/KEY: misc_feature
<223> OTHER INFORMATION: 5-prime phosphorylated loop-
      oligodeoxynecleotide

<400> SEQUENCE: 3
```

```
gggaaagctt agttttctaa gctt                                            24

<210> SEQ ID NO 4
<211> LENGTH: 24
<212> TYPE: DNA
<213> ORGANISM: Artificial
<220> FEATURE:
<223> OTHER INFORMATION: synthetic deoxyoligonucleotide
<220> FEATURE:
<221> NAME/KEY: misc_feature
<223> OTHER INFORMATION: 5-prime phosphorylated loop-
      oligodeoxynucleotide

<400> SEQUENCE: 4
gttggaattc agttttctga attc                                            24
```